United States Patent [19]

Nishiki

[11] Patent Number: 4,924,487
[45] Date of Patent: May 8, 1990

[54] X-RAY DIAGNOSTIC APPARATUS

[75] Inventor: Masayuki Nishiki, Ootawara, Japan

[73] Assignee: Kabushiki Kaisha Toshiba, Kawasaki, Japan

[21] Appl. No.: 213,965

[22] Filed: Jul. 1, 1988

[30] Foreign Application Priority Data

Jul. 3, 1987 [JP] Japan .............................. 62-165300

[51] Int. Cl.⁵ .............................................. H05G 1/64
[52] U.S. Cl. ..................................... 378/190; 378/62; 378/99; 378/116; 358/111
[58] Field of Search ................... 378/116, 190, 46, 62, 378/98, 99; 358/111

[56] References Cited

U.S. PATENT DOCUMENTS 4,670,893 6/1987 Tsuchiya ............................. 378/105

FOREIGN PATENT DOCUMENTS

3332284A1 3/1984 Fed. Rep. of Germany .
3240779A1 5/1984 Fed. Rep. of Germany .
3322687A1 1/1985 Fed. Rep. of Germany .

OTHER PUBLICATIONS

Fernseh-und Kino-Technik, 33, Feb. 1979, pp. 37–42.
Siemens AG "Klinograph 2 mit Explorator GS", MS 30/1025-Ws 9734.

Primary Examiner—Carolyn E. Fields
Assistant Examiner—David P. Porta
Attorney, Agent, or Firm—Finnegan, Henderson, Farabow, Garrett and Dunner

[57] ABSTRACT

An X-ray diagnostic apparatus has two modes, i.e., a fluoroscopy mode for displaying an X-ray fluoroscopic image, and a radiography mode which is selected in response to a radiography instruction in the fluoroscopy mode, for recording an X-ray radiographic image. X-ray fluoroscopic image data obtained by an X-ray image detector in the fluoroscopy mode is converted to a digital image signal by an A/D converter. At least a plurality of frames of digital image signals of X-ray fluoroscopic images corresponding to a period which includes an input timing of the radiography instruction are continuously stored in a fluoroscopic image memory section.

9 Claims, 4 Drawing Sheets

X-RAY DIAGNOSTIC APPARATUS

BACKGROUND OF THE INVENTION

1. Field of the Invention

The present invention relates to an X-ray diagnostic apparatus having a fluoroscopy mode for displaying an X-ray fluoroscopic image on a monitor or display, and a radiography mode for recording an X-ray radiographic image on a recording medium such as an storage phosphor or X-ray film.

2. Description of the Related Art

Figure 1:
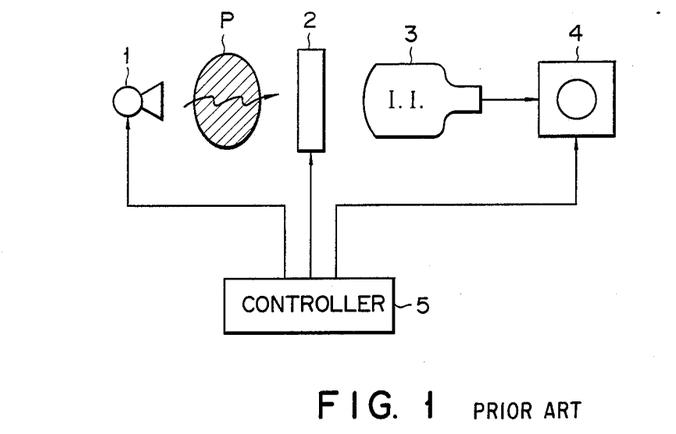
FIG. 1 is a block diagram schematically showing an arrangement of a conventional X-ray diagnostic apparatus.

An X-ray diagnostic apparatus of this type comprises X-ray generator 1, spot-shot device 2, fluoroscopic image generator 3, monitor 4, and controller 5, as shown in FIG. 1. X-ray generator 1 can generate both fluoroscopic and radiographic X-rays. Spot-shot device 2 records an X-ray radiographic image on an X-ray film or storage phosphor as a recording medium. Fluoroscopic image generator 3 includes an I.I. (image intensifier) for converting an X-ray fluoroscopic image into an optical image, and a TV (television) camera for converting the optical image output from the I.I. into an analog video signal. Thus, generator 3 converts an X-ray fluoroscopic image into an optical image, and then converts the optical image into an analog video signal. Spot-shot device 2 and generator 3 oppose X-ray generator 1 to sandwich the object to be examined (the patient) P therebetween. Monitor 4 displays a fluoroscopic image based on the analog video signal supplied from generator 3. Controller 5 controls the above-mentioned sections. The X-ray diagnostic apparatus described above has two modes, i.e., fluoroscopy and radiography modes. In the fluoroscopy mode, fluoroscopic X-rays are generated from generator 1, and an X-ray fluoroscopic image based on the fluoroscopic X-rays is converted to an analog video signal by generator 3. The analog video signal is supplied to monitor 4. Therefore, the X-ray fluoroscopic image is displayed on monitor 4 as a motion image. In the radiography mode, radiographic X-rays are generated from generator 1 in synchronism with the operation of spot-shot device 2, and an X-ray radiographic image based on the radiographic X-rays is recorded on a film or storage phosphor by spot-shot device 2.

In normal diagnostic procedures, a portion to be radiographed (to be referred to as a radiography portion hereinafter) and a radiographic timing are determined while observing an X-ray fluoroscopic image displayed on monitor 4 in the fluoroscopy mode, and a radiography switch (not shown) for inputting a radiography instruction to controller 5 is then operated. When the radiography instruction is input, the radiography mode is set, and spot radiography is made on a recording medium such as an X-ray film or storage phosphor.

However, a radiography portion and a radiographic timing requested by an operator during X-ray fluoroscopic image observation do not often coincide with those of an actually radiographed X-ray image. In an X-ray image obtained in this case, at least one of a radiography portion and a radiographic timing is different from those requested by the operator. This is for the following reason. That is, after a radiography instruction for switching from the fluoroscopy mode to the radiography mode is supplied, radiography cannot be executed before a time required for conveying a recording medium used for radiography, and a time required for achieving a high-speed rotation of a rotary anode of an X-ray tube for switching a fluoroscopic X-ray to a radiographic X-ray in generator 1 have passed. For this reason, a time lag of 1 to 2 sec is generated from when the operator operates the radiography switch until the radiographic X-rays are actually radiated.

Because of the presence of the time lag, a radiography portion makes an irregular motion or the concentration of a contrast medium falls outside a desired value, thus causing a radiography failure. In a normal case, successful radiography can be determined only after the recording medium is developed or visualized by image reading. For this reason, after a considerable time has passed from the radiography, the operator finds out that radiography has been unsuccessful. When radiography fails, if contrast radiography such as an angiography is performed, a contrast medium must be injected again, thus resulting in a heavy load on a patient. In other radiography operations, an operation for performing radiography starting from the fluoroscopy mode must be performed again, resulting in cumbersome operations and a load on a patient.

In the conventional X-ray diagnostic apparatus, a radiography portion and a radiographic timing which are set by an operator while observing an X-ray fluoroscopic image displayed on a monitor in the fluoroscopy mode do not coincide with those of an X-ray radiographic image recorded on a recording medium, e.g., a storage phosphor or X-ray film due to the presence of a time lag. Thus, diagnosis data desired by an operator cannot be obtained from an X-ray image recorded in the radiography mode.

SUMMARY OF THE INVENTION

It is an object of the present invention to provide an X-ray diagnostic apparatus capable of easily and reliably obtaining X-ray image data of a desired radiography portion at a desired radiographic timing.

An X-ray diagnostic apparatus according to the present invention has two modes, i.e., a fluoroscopy mode for displaying an X-ray fluoroscopic image, and a radiography mode, which is selected in response to a radiography instruction in the fluoroscopy mode, for recording an X-ray radiographic image. X-ray fluoroscopic image data obtained by an X-ray image detector in the fluoroscopy mode is converted into a digital image signal by an A/D converter. A plurality of frames of images corresponding to a period including an input timing of the radiography instruction of the digital image signal of the X-ray fluoroscopic image are continuously stored in a fluoroscopic image memory section.

According to the X-ray diagnostic apparatus of the present invention, a plurality of frames of digital X-ray fluoroscopic images for a period including an input timing of the radiography instruction are stored in the fluoroscopic image memory section. The stored images can be displayed on, e.g., a monitor or can be utilized as a diagnostic recorded image. Therefore, X-ray image data of a desired radiography portion at a desired radiographic timing can be obtained.

DETAILED DESCRIPTION OF THE PREFERRED EMBODIMENTS

Embodiments of an X-ray diagnostic apparatus according to the present invention will be described hereinafter with reference to the accompanying drawings.

Figure 2:
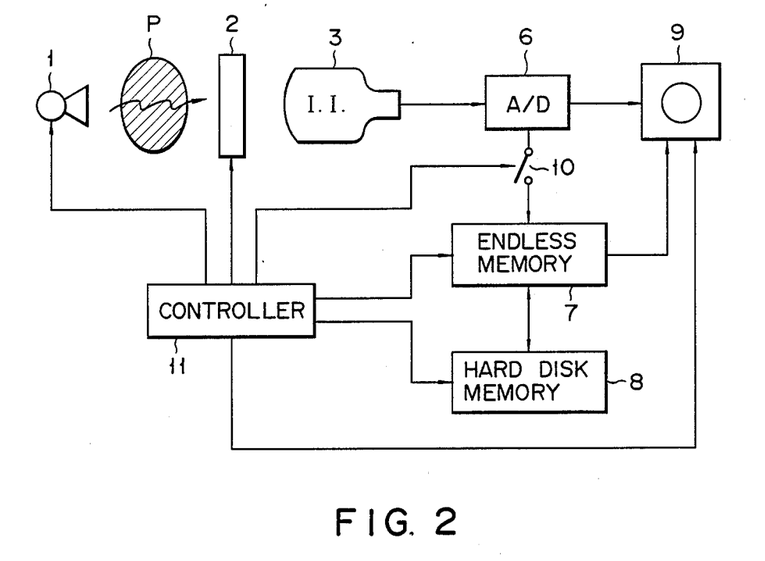
FIG. 2 is a block diagram schematically showing an arrangement of an X-ray diagnostic apparatus according to a first embodiment of the present invention.

FIG. 2 shows a schematic arrangement of an X-ray diagnostic apparatus according to a first embodiment of the present invention.

The apparatus shown in FIG. 2 comprises X-ray generator 1, spot-shot device 2, fluoroscopic image generator 3, A/D (analog-to-digital) converter 6, endless memory 7, hard disk memory 8, monitor 9, switch 10, and controller 11.

In FIG. 2, generator 1, device 2, and generator 3 are the same as those shown in FIG. 1. A/D converter 6 converts a video signal of an X-ray fluoroscopic image obtained by generator 3 into a digital signal. Endless memory 7 comprises, a semiconductor memory, for example. Endless memory 7 continuously and endlessly stores digital video data of X-ray fluoroscopic images obtained by A/D converter 6 in units of frames in the fluoroscopy mode. When data stored in hard disk memory 8 is reproduced, memory 7 serves as a buffer memory for temporarily storing digital video data of X-ray fluoroscopic images reproduced from memory 8. Hard disk memory 8 fetches and stores, from endless memory 7, digital video data of a plurality of successive frames of X-ray fluoroscopic images corresponding to a period which includes, at an intermediate point of time, an operation timing of a radiography switch (not shown) for supplying a radiography instruction to a system, that is, digital video data of a plurality of successive frames of X-ray fluoroscopic images consisting of a frame which substantially corresponds to an instance when the radiography switch is operated, frames therebefore, and frames thereafter. Monitor 9 converts, into an analog signal, digital data of X-ray fluoroscopic images respectively supplied from A/D converter 6 in the fluoroscopy mode and from memory 7 upon reproduction of data stored in memory 8, and displays images based on the analog signal. Switch 10 is used for switching an enable/disable state of updating write access of X-ray fluoroscopic images into memory 7. Controller 11 controls the above-mentioned sections.

The operation of the X-ray diagnostic apparatus with the above arrangement will hereinafter be described.

An operator determines a radiography portion and a radiographic timing while observing an X-ray fluoroscopic image displayed on monitor 9. In this case, switch 10 is kept on, and memory 7 continuously and endlessly stores, in units of frames, digital video data of X-ray fluoroscopic images output from A/D converter 6. The storage contents of memory 7 are updated for every predetermined period of time, and memory 7 always stores a plurality of the most recent successive frames of video data.

Figure 3:
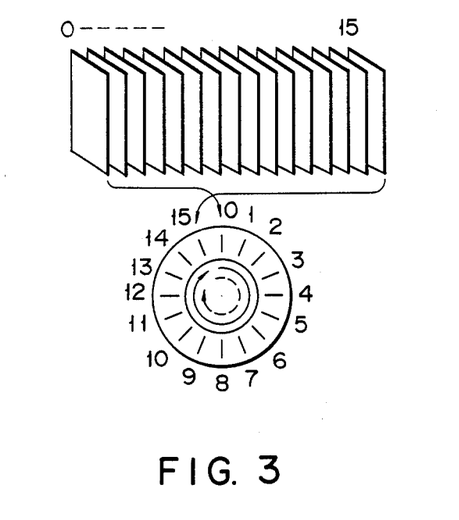
FIG. 3 is a view for explaining the principle of an endless memory used in the apparatus shown in FIG. 2.

FIG. 3 illustrates, in principle, the storage contents of memory 7. For example, a loop consisting of 16 frame memories numbered from 0 to 15 is used. A given frame of data is stored in memory No. 0, and the subsequent frame of data is stored in memory No. 1, and so forth. After data has been stored in memory No. 15, the content of memory No. 0 is then updated to store a new frame of data. Such operation can be achieved by cyclically addressing normal memory, using a count value of a ring counter, for example.

Figure 4:
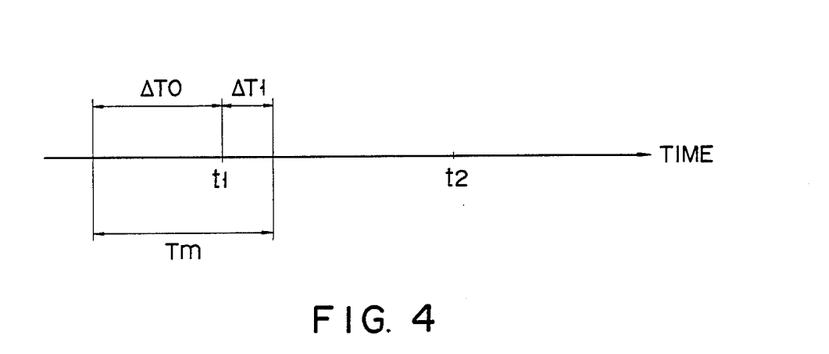
FIG. 4 is a view for explaining operation timings of radiography and fluoroscopic image storage in the apparatus shown in FIG. 2.

As shown in FIG. 4, when an operator turns on the radiography switch at time t1 to set the radiography mode, the radiography instruction is input to a system, and radiographic X-rays are actually radiated at time t2 so that the spot-shot device 2 performs radiographing on the recording medium. The following operation is accordingly performed in this apparatus. After a predetermined period of time $\Delta T1$ has elapsed from turned-on time t1 of the radiography switch, switch 10 is turned off by controller 11, so that write access to memory 7 is inhibited. As a result, if the capacity of memory 7 corresponds to image data for time period Tm, digital data of a plurality of frames of fluoroscopic images during a time period from a time $(t1 - \Delta T0)$, which precedes time t1 by time period $\Delta T0$ $(= Tm - \Delta T1)$, to a time $(t1 + \Delta T1)$, which follows time t1 by time period $\Delta T1$, are stored in memory 7. Note that after the radiography switch has been turned on, normal radiation (continuous or intermittent radiation) of fluoroscopic X-rays must be carried out for time period $\Delta T1$. If a radiography instruction is received when the system is set in the fluoroscopy mode, the fluoroscopic X-rays radiated are caused to stop a short period of time thereafter. When time period $\Delta T1$ is to be prolonged, a time period from an input timing of the radiography instruction to a stop timing of the fluoroscopic X-rays is prolonged accordingly. As stated above, a certain time period is necessary from the time the radiography instruction is supplied in the fluoroscopy mode until radiographic X-rays are radiated. The fluoroscopic X-rays can be radiated to a time immediately before the radiographic X-rays are radiated.

After the write access has been inhibited, the storage contents of memory 7 are immediately transferred to memory 8. Thereafter, switch 10 is turned on again so that the fluoroscopy mode is repeated and write access to memory 7 can be restarted.

The reason why a plurality of X-ray fluoroscopic image frames are recorded before and after time t1 recorded will be explained below.

When an operator, e.g., a doctor, operates the radiography switch while observing an X-ray fluoroscopic image displayed on monitor 9, a desired radiographic timing is often present in a period slightly before the instance when he depresses the radiography switch. In contrast to this, the operator may operate the radiography switch previous to a desired timing. Thus, when a plurality of frames of X-ray fluoroscopic images for a period before and after time t1 are recorded, the operator can then obtain an X-ray image at a radiographic timing which he desires.

The contents stored in memory 8 are displayed as follows.

A "reference motion image" key for displaying the contents stored in memory 8 is arranged on a keyboard of a console (not shown) (the radiography switch for inputting the radiography instruction may also be arranged on this console). A doctor carries out diagnosis after radiographing. Since a doctor performs diagnosis using only a radiographic image, he performs it while observing an image obtained from the radiographed X-ray film or storage phosphor. The "reference animation" key is operated at any time when necessary. When the "reference motion image" key is depressed, a plurality of X-ray fluoroscopic image frames stored in memory 8 are sequentially supplied to monitor 9 under the control of controller 11, and are repetitively and continuously displayed on monitor 9. In this case, the display speed or order (i.e., forward or reverse order) as well as freeze display (stop motion) of the X-ray fluoroscopic images may be controlled in the apparatus.

In this apparatus, during diagnosis of an X-ray image radiographed on the recording medium, X-ray fluoroscopic images for a period before and after time t1, which are stored in memory 8, can be displayed (the stored images may be subjected to appropriate image processing in order to improve their diagnostic performance). Therefore, if X-ray radiography fails, diagnosis can still be carried out with reference to the X-ray fluoroscopic images for a period before and after time t1. In many cases, a satisfactory practical diagnosis can be performed, and X-ray radiography need not be performed again. Even in the case where X-ray radiography is successful, the displaying of X-ray fluoroscopic images for a period before and after time t1 can effectively assist appropriate diagnosis. Thus, through use of the apparatus of the present invention, a more appropriate diagnosis can be made as compared with the case wherein a conventional apparatus is used.

In the above embodiment, endless memory 7 is commonly used as a buffer memory upon reproduction of the contents of hard disk memory 8. Alternatively, a reproduction buffer memory may be provided in addition to endless memory 7.

An X-ray diagnostic apparatus according to a second embodiment of the present invention will be described with reference to FIG. 5.

Figure 5:
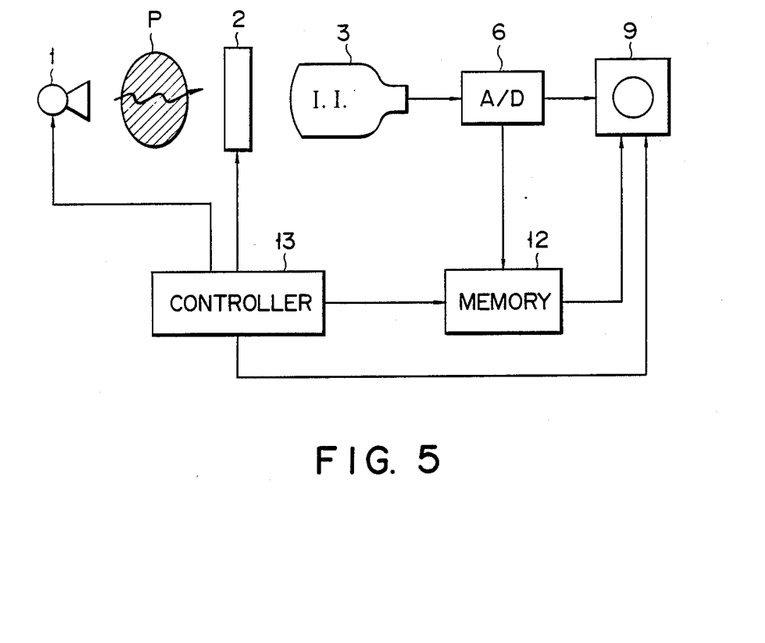
FIG. 5 is a block diagram schematically showing an X-ray diagnostic apparatus according to a second embodiment of the present invention.

In the apparatus shown in FIG. 5, all the fluoroscopic images are stored in large-capacity memory 12 comprising a semiconductor memory, without the use of an endless memory. Based on a timing signal supplied through controller 13 when a radiography instruction is input, some mark or data associated with radiography, e.g., an ID (identification) number of a patient or a radiography count number is assigned to video data corresponding to a frame, stored at time t1, of the stored images.

In the apparatus shown in FIG. 5, during diagnosis, an image radiographed at time t1 can be quickly retrieved based on the mark or data associated with radiography, and X-ray fluoroscopic images at time t1 and at timings therebefore and thereafter can also be quickly retrieved to be effectively used for diagnosis using an X-ray image radiographed on an X-ray film.

Note that a digital video tape recorder (digital VTR) capable of performing digital recording in real time may be used in place of memory 12 shown in FIG. 5.

In each of the above embodiments, X-ray fluoroscopic images are stored in a memory, and are displayed on a monitor. However, hard copies of stored X-ray fluoroscopic images may be directly formed.

In recent years, along with development of a high-performance I.I.-TV system, attempts have been made to use the I.I.-TV system in still X-ray image radiography by using radiographic X-rays. An X-ray diagnostic apparatus according to a third embodiment of the present invention wherein the present invention is applied to such a system, will hereinafter be described with reference to FIG. 6.

Figure 6:
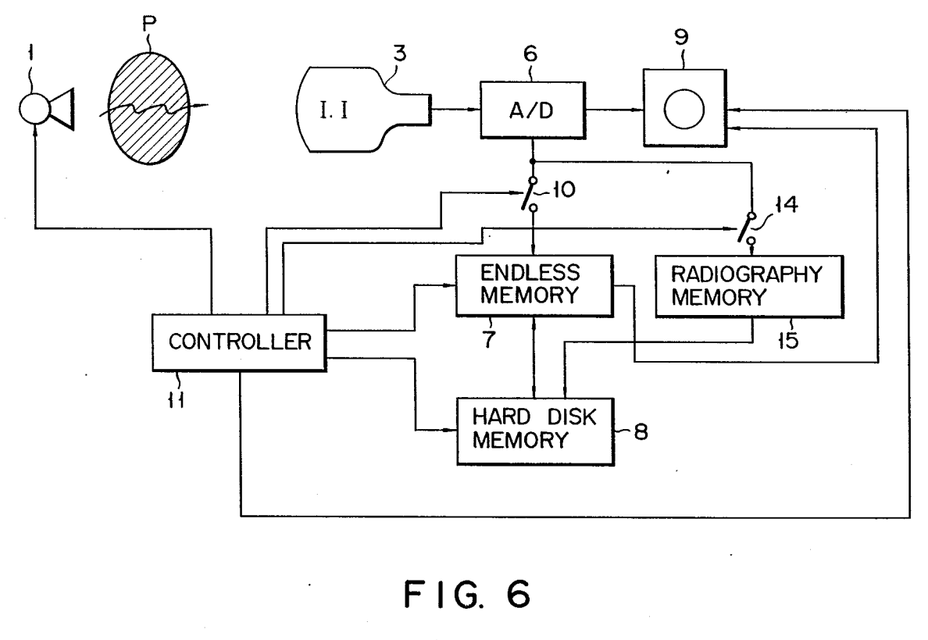
FIG. 6 is a block diagram schematically showing an X-ray diagnostic apparatus according to a third embodiment of the present invention.

In the arrangement of FIG. 6, spot-shot device 2 shown in FIG. 2, is not used, and radiography memory switch 14 and radiography memory 15 controlled by controller 11 are added in the place of spot-shot device 2.

In the apparatus shown in FIG. 6, the storage operation for the X-ray fluoroscopic images before and after the radiography instruction is the same as that in the apparatus of FIG. 2, except in the following points. That is, in the apparatus of FIG. 6, in the radiography mode, radiography memory 15 is selected by memory switch 14 controlled by controller 11, and after completion of radiography, the images are stored in hard disk memory 8.

The difference between X-ray radiographic and fluoroscopic images will be explained. In the case of the X-ray radiographic image, the X-ray dose radiated per frame must be considerably higher than the X-ray does required for the X-ray fluoroscopic image so that a diagnosis must be made using only one still image.

Figure 7:
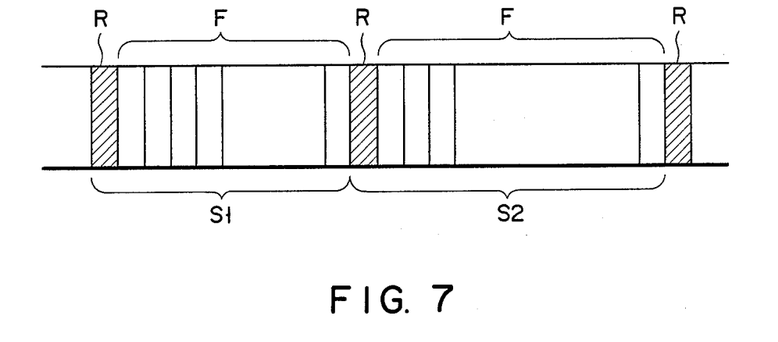
FIG. 7 is a view for explaining a recording format of image data in a hard disk memory in the apparatus shown in FIG. 6.

If image data in the hard disk memory in FIG. 6 is stored in accordance with the format shown in FIG. 7, it is convenient for the later retrieval operation. More specifically, X-ray radiographic image data R corresponding to first radiographic timing S1 is followed by X-ray fluoroscopic image data F corresponding to timing S1. After these data follow image data R and F corresponding to second radiographic timing S2.

"Reference motion image" and "next radiographic image" keys for displaying the content stored in hard disk memory 8 are arranged on a keyboard of a console (not shown). After radiographing, diagnosis is carried out by operating the keyboard. Since diagnosis is made using only a radiographic image, diagnosis can be performed by only depressing the "next radiographic image" key. The "reference motion image" key is used as needed or for reference at an arbitrary timing. When the "reference motion image" key is depressed, an X-ray fluoroscopic image having the same timing as that of the currently displayed X-ray radiographic image is displayed as a motion image on monitor 9. In this case, X-ray radiographic and fluoroscopic images may be simultaneously displayed on a screen of monitor 9 which is divided into two portions or may be alternately displayed upon key operation. Note that the X-ray radiographic image may be displayed on a different monitor than that used for displaying the X-ray fluoroscopic image.

Various other changes and modifications may be made within the spirit and scope of this invention.

What is claimed is:

1. An X-ray diagnostic apparatus comprising:
X-ray image detecting means, having a fluoroscopy mode and a radiography mode for, in the fluoroscopy mode, radiating fluoroscopic X-rays onto an object being examined so as to detect X-ray fluoroscopic image data of the object being examined, and for, in the radiography mode, radiating radiographic X-rays onto the object being examined so as to detect X-ray radiographic image data of the object being examined, the radiography mode being selected in response to a radiography instruction applied in the fluoroscopy mode;

display means for displaying the X-ray fluoroscopic image data obtained by said X-ray image detecting means in the fluoroscopy mode;

radiographic image recording means for recording the X-ray radiographic image data obtained by said X-ray image detecting means in the radiography mode;

A/D (analog-to-digital) conversion means for converting the X-ray fluoroscopic image data obtained by said X-ray image detecting means in the fluoroscopy mode into a digital signal; and fluoroscopic image storage means for continuously storing a plurality of frames of digital image signals of X-ray fluoroscopic images obtained by said A/D conversion means in correspondence with a period which includes an input timing of the radiography instruction.

2. An X-ray diagnostic apparatus comprising:

X-ray image detecting means, having a fluoroscopy mode and a radiography mode for, in the fluoroscopy mode, radiating fluoroscopic X-rays onto an object being examined so as to detect X-ray fluoroscopic image data of the object being examined, and for, in the radiography mode, radiating radiographic X-rays onto the object being examined so as to detect X-ray radiographic image data of the object being examined, the radiography mode being selected in response to a radiography instruction applied in the fluoroscopy mode;

display means for displaying the X-ray fluoroscopic image data obtained by said X-ray image detecting means in the fluoroscopy mode;

radiographic image recording means for recording the X-ray radiographic image data obtained by said X-ray image detecting means in the radiography mode;

A/D (analog-to-digital) conversion means for converting the X-ray fluoroscopic image data obtained by said X-ray image detecting means in the fluoroscopy mode into a digital signal; and fluoroscopic image storage means for continuously storing at least a plurality of frames of digital image signals of X-ray fluoroscopic images obtained by said A/D conversion means in correspondence with a period which includes an input timing of the radiography instruction, said fluoroscopic image storage means comprising updating storage means for continuously updating and storing a plurality of the most recent frames, and storage control means responsive to the radiography instruction, for interrupting write access to said updating storage means after a predetermined period of time has elapsed from the input timing of the radiography instruction until the fluoroscopic X-rays have stopped.

3. An X-ray diagnostic apparatus comprising:

X-ray image detecting means, having a fluoroscopy mode and a radiography mode for, in the fluoroscopy mode, radiating fluoroscopic X-rays onto an object being examined so as to detect X-ray fluoroscopic image data of the object being examined, and for, in the radiography mode, radiating radiographic X-rays onto the object being examined so as to detect X-ray radiographic image data of the object being examined, the radiography mode being selected in response to a radiography instruction applied in the fluoroscopy mode;

display means for displaying the X-ray fluoroscopic image data obtained by said X-ray image detecting means in the fluoroscopy mode;

radiographic image recording means for recording the X-ray radiographic image data obtained by said X-ray image detecting means in the radiography mode;

A/D (analog-to-digital) conversion means for converting the X-ray fluoroscopic image data obtained by said X-ray image detecting means in the fluoroscopy mode into a digital signal; and fluoroscopic image storage means for continuously storing at least a plurality of frames of digital image signals of X-ray fluoroscopic images obtained by said A/D conversion means in correspondence with a period which includes an input timing of the radiography instruction, said fluoroscopic image storage means comprising updating storage means for continuously updating and storing a plurality of the most recent frames, storage control means responsive to the radiography instruction, for interrupting write access to said updating storage means after a predetermined period of time has elapsed from the input timing of the radiography instruction until fluoroscopic X-rays have stopped, and auxiliary storage means for fetching and storing a storage content of said updating storage means.

4. An apparatus according to claim 1, wherein said fluoroscopic image storage means includes large-capacity storage means for storing all the frames during a fluoroscopy mode period.

5. An apparatus according to claim 1, wherein said fluoroscopic image storage means includes means for supplying a storage content to said display means for display as requested.

6. An apparatus according to claim 1, wherein said X-ray image detecting means includes means for supplying a storage content to said display means for display as requested.

7. An apparatus according to claim 1, wherein said radiographic image recording means includes film radiography means for recording the X-ray radiographic image on an X-ray film.

8. An apparatus according to claim 7, wherein said film radiography means comprises a spot-shot device.

9. An apparatus according to claim 1, wherein said radiographic image recording means includes digital image signal recording means for converting the X-ray radiographic image into a digital signal and recording the digital signal on a recording medium.

* * * * *

UNITED STATES PATENT AND TRADEMARK OFFICE
CERTIFICATE OF CORRECTION

PATENT NO. : 4,924,487
DATED : May 08, 1990
INVENTOR(S) : Masayuki NISHIKI

It is certified that error appears in the above-identified patent and that said Letters Patent is hereby corrected as shown below:

In the Claims:

Claim 1, Column 6, Line 62, insert --a-- after radiating;

Claim 1, Column 6, Line 62, change "X-rays" to --X-ray--;

Claim 1, Column 6, Line 65, insert --a-- after radiating;

Claim 1, Column 6, Line 66, change "X-rays" to --X-ray--;

Claim 2, Column 7, Line 23, insert --a-- after radiating;

Claim 2, Column 7, Line 23, change "X-rays" to --X-ray--;

Claim 2, Column 7, Line 26, insert --a-- after radiating;

Claim 2, Column 7, Line 27, change "X-rays" to --X-ray--;

Claim 3, Column 7, Line 61, insert --a-- after radiating;

UNITED STATES PATENT AND TRADEMARK OFFICE
CERTIFICATE OF CORRECTION

PATENT NO.  : 4,924,487
DATED       : May 08, 1990
INVENTOR(S) : Masayuki NISHIKI It is certified that error appears in the above-identified patent and that said Letters Patent is hereby corrected as shown below:

In the Claims:

Claim 3, Column 7, Line 61, change "X-rays" to --X-ray--;

Claim 3, Column 8, Line 3, insert --a-- after radiating;

Claim 3, Column 8, Line 4, change "X-rays" to --X-ray--;

Claim 3, Column 8, Line 33, insert --the-- after until;

Claim 3, Column 8, Line 33, change "X-rays" to --X-ray--.

Signed and Sealed this

Fourth Day of August, 1992

Attest:

DOUGLAS B. COMER

*Attesting Officer*     *Acting Commissioner of Patents and Trademarks*